(12) United States Patent
Cazares et al.

(10) Patent No.: US 8,700,138 B2
(45) Date of Patent: *Apr. 15, 2014

(54) METHODS AND DEVICES FOR DETERMINATION OF ARRHYTHMIA RATE ZONE THRESHOLDS

(75) Inventors: Shelley M. Cazares, Minneapolis, MN (US); Carlos A. Ricci, Apple Valley, MN (US); Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 892 days.

This patent is subject to a terminal disclaimer.

(21) Appl. No.: 12/545,364

(22) Filed: Aug. 21, 2009

(65) Prior Publication Data

US 2009/0312813 A1    Dec. 17, 2009

Related U.S. Application Data

(62) Division of application No. 11/506,253, filed on Aug. 18, 2006, now Pat. No. 7,580,741.

(51) Int. Cl.
*A61B 5/04* (2006.01)
(52) U.S. Cl.
USPC ............. 600/515; 600/518; 607/4; 607/5; 607/14
(58) Field of Classification Search
USPC ................. 600/515; 607/4, 5, 9, 14
See application file for complete search history.

(56) References Cited

U.S. PATENT DOCUMENTS

| | | | |
|---|---|---|---|
| 4,475,551 A * | 10/1984 | Langer et al. ............ 607/5 |
| 4,550,221 A | 10/1985 | Mabusth | |
| 4,686,332 A | 8/1987 | Greanias et al. | |
| 4,878,497 A | 11/1989 | Callaghan et al. | |
| 5,036,849 A | 8/1991 | Hauck et al. | |
| 5,224,486 A | 7/1993 | Lerman et al. | |
| 5,231,990 A | 8/1993 | Gauglitz | |

(Continued)

FOREIGN PATENT DOCUMENTS

| | | |
|---|---|---|
| EP | 0560569 | 9/1993 |
| EP | 1038498 | 9/2000 |

(Continued)

OTHER PUBLICATIONS

Wilkoff BL, et al., Preventing Shocks after ICD Implantation: Can a Strategy of Standardized ICD Programming Match Physician Tailored? Late Breaking Trials, HRS 2005.

(Continued)

*Primary Examiner* — Carl H Layno
*Assistant Examiner* — Jennifer Ghand
(74) *Attorney, Agent, or Firm* — Brooks, Cameron & Huebsch, PLLC

(57) ABSTRACT

Approaches for determining threshold values for one or more arrhythmia rate zones and/or the number of rate zones are described. A probability function for heart rate is determined using collected and measured heart rate values. One or more heart rate probability values are selected. Thresholds for arrhythmia rate zones are determined from the probability function based on the selected probability values. Determining the rate zone thresholds may involve determining a threshold for a lower rate limit and/or determining one or more tachyarrhythmia rate zone thresholds. The number of rate zones may also be determined based on the probability function.

19 Claims, 8 Drawing Sheets

(56) References Cited

U.S. PATENT DOCUMENTS

| | | |
|---|---|---|
| 5,271,411 A | 12/1993 | Ripley et al. |
| 5,284,136 A | 2/1994 | Hauck et al. |
| 5,299,118 A | 3/1994 | Martens et al. |
| 5,301,677 A | 4/1994 | Hsung |
| 5,312,445 A | 5/1994 | Nappholz et al. |
| 5,313,953 A | 5/1994 | Yomtov et al. |
| 5,324,310 A | 6/1994 | Greeninger et al. |
| 5,331,966 A | 7/1994 | Bennett et al. |
| 5,342,402 A | 8/1994 | Olson et al. |
| 5,350,410 A | 9/1994 | Kleks et al. |
| 5,388,578 A | 2/1995 | Yomtov et al. |
| 5,411,031 A | 5/1995 | Yomtov |
| 5,411,533 A | 5/1995 | Dubreuil |
| 5,431,693 A | 7/1995 | Schroeppel |
| 5,443,485 A | 8/1995 | Housworth et al. |
| 5,458,620 A | 10/1995 | Adams et al. |
| 5,545,186 A | 8/1996 | Olson et al. |
| 5,605,158 A | 2/1997 | Snell |
| 5,620,466 A | 4/1997 | Haefner et al. |
| 5,626,620 A | 5/1997 | Kieval et al. |
| 5,662,688 A | 9/1997 | Haefner et al. |
| 5,674,254 A | 10/1997 | van Krieken |
| 5,683,431 A | 11/1997 | Wang |
| 5,697,959 A | 12/1997 | Poore |
| 5,704,365 A | 1/1998 | Albrecht et al. |
| 5,722,416 A | 3/1998 | Swanson et al. |
| 5,735,882 A | 4/1998 | Rottenberg et al. |
| 5,755,737 A | 5/1998 | Prieve et al. |
| 5,779,645 A | 7/1998 | Olson et al. |
| 5,803,084 A | 9/1998 | Olson |
| 5,836,971 A | 11/1998 | Starkweather |
| 5,844,506 A | 12/1998 | Binstead |
| 5,855,593 A | 1/1999 | Olson et al. |
| 5,861,013 A | 1/1999 | Peck et al. |
| 5,871,512 A | 2/1999 | Hemming et al. |
| 5,873,897 A | 2/1999 | Armstrong et al. |
| 5,873,898 A | 2/1999 | Hemming et al. |
| 5,882,352 A | 3/1999 | Duncan et al. |
| 6,038,474 A | 3/2000 | Zhu et al. |
| 6,044,298 A | 3/2000 | Salo et al. |
| 6,084,253 A | 7/2000 | Johnson et al. |
| 6,091,990 A | 7/2000 | Hsu et al. |
| 6,101,416 A | 8/2000 | Sloman |
| 6,115,628 A | 9/2000 | Stadler et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |
| 6,175,766 B1 | 1/2001 | Bornzin et al. |
| 6,221,011 B1 | 4/2001 | Bardy |
| 6,226,551 B1 | 5/2001 | Zhu et al. |
| 6,230,055 B1 | 5/2001 | Sun et al. |
| 6,253,102 B1 | 6/2001 | Hsu et al. |
| 6,259,947 B1 | 7/2001 | Olson et al. |
| 6,266,554 B1 | 7/2001 | Hsu et al. |
| 6,267,778 B1 | 7/2001 | Cohen |
| 6,280,380 B1 | 8/2001 | Bardy |
| 6,301,503 B1 | 10/2001 | Hsu et al. |
| 6,324,421 B1 | 11/2001 | Stadler et al. |
| 6,324,427 B1 | 11/2001 | Florio |
| 6,345,201 B1 | 2/2002 | Sloman et al. |
| 6,368,284 B1 | 4/2002 | Bardy |
| 6,393,316 B1 | 5/2002 | Gillberg et al. |
| 6,409,675 B1 | 6/2002 | Turcott |
| 6,418,340 B1 | 7/2002 | Conley et al. |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,449,504 B1 | 9/2002 | Conley et al. |
| 6,456,880 B1 | 9/2002 | Park et al. |
| 6,456,881 B1 | 9/2002 | Bornzin et al. |
| 6,477,422 B1 | 11/2002 | Splett |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,505,067 B1 | 1/2003 | Lee et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,564,106 B2 | 5/2003 | Guck et al. |
| 6,597,951 B2 | 7/2003 | Kramer et al. |
| 6,618,619 B1 | 9/2003 | Florio et al. |
| 6,622,046 B2 | 9/2003 | Fraley et al. |
| 6,625,490 B1 | 9/2003 | McClure et al. |
| 6,631,290 B1 | 10/2003 | Guck et al. |
| 6,654,637 B2 | 11/2003 | Rouw et al. |
| 6,690,967 B2 | 2/2004 | Meij |
| 6,708,058 B2 | 3/2004 | Kim et al. |
| 6,725,085 B2 | 4/2004 | Schwartzman et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,856,835 B2 | 2/2005 | Bardy et al. |
| 6,881,192 B1 | 4/2005 | Park |
| 6,885,893 B1 | 4/2005 | Lu |
| 6,888,538 B2 | 5/2005 | Ely et al. |
| 6,889,079 B2 | 5/2005 | Bocek et al. |
| 6,904,315 B2 | 6/2005 | Panken et al. |
| 6,925,330 B2 | 8/2005 | Kleine |
| 6,944,495 B2 | 9/2005 | MacAdam et al. |
| 6,950,702 B2 | 9/2005 | Sweeney |
| 6,952,610 B2 | 10/2005 | Ostroff |
| 6,959,214 B2 | 10/2005 | Pape et al. |
| 6,961,613 B2 | 11/2005 | Bjorling et al. |
| 6,973,350 B1 | 12/2005 | Levine et al. |
| 6,975,904 B1 | 12/2005 | Sloman |
| 6,988,003 B2 | 1/2006 | Bardy et al. |
| 6,993,379 B1 | 1/2006 | Kroll |
| 6,999,817 B2 | 2/2006 | Park et al. |
| 7,006,869 B2 | 2/2006 | Bradley |
| 7,027,861 B2 | 4/2006 | Thompson |
| 7,039,459 B2 | 5/2006 | Bardy |
| 7,043,299 B2 | 5/2006 | Erlinger |
| 7,065,400 B2 | 6/2006 | Schechter |
| 7,065,410 B2 | 6/2006 | Bardy et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,103,404 B2 | 9/2006 | Stadler et al. |
| 7,113,823 B2 | 9/2006 | Yonce et al. |
| 7,117,036 B2 | 10/2006 | Florio |
| 7,120,495 B2 | 10/2006 | Bardy et al. |
| 7,123,954 B2 | 10/2006 | Narayan et al. |
| 7,127,290 B2 | 10/2006 | Girouard |
| 7,139,610 B2 | 11/2006 | Ferek-Petric |
| 7,146,206 B2 | 12/2006 | Glass et al. |
| 7,177,689 B2 | 2/2007 | Ternes et al. |
| 7,191,003 B2 | 3/2007 | Greenhut et al. |
| 7,191,004 B2 | 3/2007 | Kim et al. |
| 7,194,309 B2 | 3/2007 | Ostroff et al. |
| 7,203,542 B2 | 4/2007 | Obel |
| 7,203,543 B2 | 4/2007 | Meyer et al. |
| 7,212,862 B2 | 5/2007 | Park et al |
| 7,225,021 B1 | 5/2007 | Park et al. |
| 7,228,173 B2 | 6/2007 | Cazares |
| 7,236,819 B2 | 6/2007 | Brockway et al. |
| 7,242,978 B2 | 7/2007 | Cao |
| 7,245,962 B2 | 7/2007 | Ciaccio et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,319,900 B2 | 1/2008 | Kim et al. |
| 7,457,664 B2 | 11/2008 | Zhang et al. |
| 7,477,932 B2 | 1/2009 | Lee |
| 7,558,628 B2 | 7/2009 | Yonce et al. |

(56) References Cited

U.S. PATENT DOCUMENTS

| | | | |
|---|---|---|---|
| 7,580,741 | B2 | 8/2009 | Cazares et al. |
| 7,818,056 | B2 | 10/2010 | Kim et al. |
| 2002/0082658 | A1 | 6/2002 | Heinrich et al. |
| 2002/0095184 | A1 | 7/2002 | Bardy et al. |
| 2002/0107544 | A1 | 8/2002 | Ostroff et al. |
| 2002/0120311 | A1 | 8/2002 | Lindh et al. |
| 2003/0212436 | A1 | 11/2003 | Brown |
| 2004/0064159 | A1 | 4/2004 | Hoijer et al. |
| 2004/0172065 | A1 | 9/2004 | Sih et al. |
| 2004/0215240 | A1 | 10/2004 | Lovett et al. |
| 2004/0215277 | A1 | 10/2004 | Oosterhoff |
| 2004/0230128 | A1 | 11/2004 | Brockway et al. |
| 2004/0239650 | A1 | 12/2004 | Mackey |
| 2004/0243014 | A1 | 12/2004 | Lee et al. |
| 2004/0260351 | A1 | 12/2004 | Holmstrom et al. |
| 2005/0004486 | A1 | 1/2005 | Glass et al. |
| 2005/0004612 | A1 | 1/2005 | Scholten et al. |
| 2005/0038478 | A1 | 2/2005 | Klepfer et al. |
| 2005/0131477 | A1 | 6/2005 | Meyer et al. |
| 2005/0131478 | A1 | 6/2005 | Kim et al. |
| 2005/0137485 | A1 | 6/2005 | Cao |
| 2005/0288600 | A1 | 12/2005 | Zhang et al. |
| 2006/0047319 | A1 | 3/2006 | Bruhns et al. |
| 2006/0069322 | A1 | 3/2006 | Zhang et al. |
| 2006/0074331 | A1 | 4/2006 | Kim et al. |
| 2006/0111747 | A1 | 5/2006 | Cazares et al. |
| 2006/0111751 | A1 | 5/2006 | Cazares |
| 2006/0116593 | A1 | 6/2006 | Zhang et al. |
| 2006/0129194 | A1 | 6/2006 | Zhang |
| 2006/0129196 | A1 | 6/2006 | Dong et al. |
| 2006/0247695 | A1 | 11/2006 | Stalsberg et al. |
| 2006/0253043 | A1 | 11/2006 | Zhang et al. |
| 2006/0253044 | A1 | 11/2006 | Zhang et al. |
| 2006/0253164 | A1 | 11/2006 | Zhang et al. |
| 2008/0004665 | A1 | 1/2008 | McCabe et al. |
| 2008/0071182 | A1 | 3/2008 | Cazares |
| 2008/0125824 | A1 | 5/2008 | Sauer |
| 2009/0312813 | A1 | 12/2009 | Cazares |

FOREIGN PATENT DOCUMENTS

| | | |
|---|---|---|
| EP | 1291038 | 3/2003 |
| WO | WO9217240 | 10/1992 |
| WO | WO9220402 | 11/1992 |
| WO | WO0240097 | 5/2002 |
| WO | WO0247761 | 6/2002 |
| WO | WO02087696 | 11/2002 |
| WO | WO03003905 | 1/2003 |
| WO | WO03028550 | 4/2003 |
| WO | WO2004026398 | 4/2004 |
| WO | WO2005058412 | 6/2005 |
| WO | WO2005089865 | 9/2005 |
| WO | WO2006065707 | 6/2006 |
| WO | WO2008005270 | 1/2008 |

OTHER PUBLICATIONS

File History for U.S. Appl. No. 11/643,220, 274 pages.
File History for U.S. Appl. No. 11/715,125, 245 pages.
File History for U.S. Appl. No. 11/643,220, 312 pages.
Acar et al., "SVD-based on-line exercise ECG signal orthogonalization", IEEE Transactions on Biomedical Engineering, vol. 46, No. 3, (Mar. 1999). Abstract only.
Belouchrani et al., "Blind Source Separation Based on Time-Frequency Signal Representations", IEEE Transactions on Signal Processing, vol. 46, No. 11, pp. 2888-2897 (Nov. 1998).
Cohen et al. "Capture Management Efficacy in children and young adults with endocardial and unipolar epicardial systems", Europace, vol. 6, pp. 248-255 (2004).
Comon, "Independent component analysis, A new concept?", Signal Processing, vol. 36, No. 3, pp. 287-314, (Apr. 1994).
Gallois, et al., "Multi-Channel Analysis of the EEG Signals and Statistic Particularities for Epileptic Seizure Forecast", Second Joint EMBS/BMES Conference, pp. 208-215 (Oct. 23-26, 2002).
Gradaus et al., "Nonthoracotomy Implantable Cardioverter Defibrillator Placement in Children: Use of a Subcutaneous Array Leads and Abdominally Placed Implantable Cardioverter Defibrillators in Children", J. of Cardiovascular Electrophysiology, vol. 12, No. 3, pp. 356-360 (Mar. 2001).
Hyvärinen et al., "Independent Component Analysis: A Tutorial", Helsinski Univ. of Technology, (Apr. 1999).
Kolettis et al., "Submammary Implantation of a Cardioverter-Defibrillator with a Nonthoractomy Lead System", Am. Heart J., vol. 126, pp. 1222-1223 (Nov. 1993).
Krahn et al. "Recurrent syncope. Experience with an implantable loop record", Cardiol. Clin., vol. 15(2), (May 1997), pp. 316-326.
Leng et al., "Lead Configuration for Defibrillator Implantation in a Patient with Congenital Heart Disease and a Mechanical Prosthetic Tricuspid Valve", PACE, vol. 24, No. 8, pp. 1291-1292 (Aug. 2001).
Park et al., "Use of an Implantable Cardioverter Defibrillator in an Eight-Month-Old Infant with Ventricular Fibrillation Arising from a Myocardial Fibroma", PACE, vol. 22, No. 1, pp. 138-139 (Jan. 1999).
Rieta, et al., "Atrial Activity Extraction Based on Blind Source Separation as an Alternative to QRST Cancellation for Atrial Fibrillation Analysis", Computers in Cardiology, vol. 27, pp. 69-72 (2000).
Schuder et al., "Transthoracic Ventricular Defibrillation in the Dog with Truncated and Untruncated Exponential Stimuli", IEEE Transitions on Bio-Medical Engineering, vol. BME-18, No. 6, pp. 410-415, (Nov. 1971).
Schuder et al., "Experimental Ventricular Defibrillation with an Automatic and Completely Implanted System", Trans. Am. Soc. Artif. Int. Organs, vol. 16, pp. 207-212 (1970).
Schuder et al., "Ventricular Defibrillation in the Dog Using Implanted and Partially Implanted Electrode Systems", Am. J. of Cardiology, vol. 33, pp. 243-247 (Feb. 1974).
Smits et al., "Defibrillation Threshold (DFT) Model of a Fully Subcutaneous ICD System", Europace Supplements, vol. 2, at col. 778, p. B83, (Jun. 2001).
Splett et al. "Determination of Pacing Capture in Implantable Defibrillators: Benefit of Evoked Response Detection Using RV Coil to Can Vector," PACE, vol. 23, pp. 1645-1650, (2000).
Zarzoso et al., "Blind Separation of Independent Sources for Virtually Any Source Probability Density Function", IEEE Transactions on Signal Processing, vol. 47, No. 9, pp. 2419-2432 (Sep. 1999).
Zarzoso et al., "Noninvasive Fetal Electrocardiogram Extraction: Blind Separation Versus Adaptive Noise Cancellation", IEEE Transactions on Biomedical Engineering, vol. 48, No. 1, pp. 12-18 (Jan. 2001).
Office Action dated Jun. 9, 2010 from U.S. Appl. No. 11/643,220, 10 pages.
Office Action Response dated Apr. 19, 2010 from U.S. Appl. No. 11/643,220, 11 pages.
Office Action dated Mar. 4, 2010 from U.S. Appl. No. 11/643,220, 3 pages.
Office Action Response dated Feb. 17, 2010 from U.S. Appl. No. 11/643,220, 10 pages.
Office Action dated Nov. 17, 2009 from U.S. Appl. No. 11/643,220, 10 pages.
Office Action Response dated Jul. 20, 2009 from U.S. Appl. No. 11/643,220, 13 pages.
Interview Summary dated Jun. 26, 2009 from U.S. Appl. No. 11/643,220, 4 pages.
Office Action dated Mar. 31, 2009 from U.S. Appl. No. 11/643,220, 7 pages.
Notice of Allowance dated May 1, 2009 from U.S. Appl. No. 11/506,253, 9 pages.
Office Action Response dated Feb. 24, 2009 from U.S. Appl. No. 11/506,253, 8 pages.
Office Action dated Nov. 7, 2008 from U.S. Appl. No. 11/506,253, 9 pages.
Office Action Response dated Mar. 8, 2010 from U.S. Appl. No. 11/715,128, 15 pages.
Office Action dated Feb. 22, 2010 from U.S. Appl. No. 11/715,128, 7 pages.
Office Action Response dated Feb. 3, 2010 from U.S. Appl. No. 11/715,128, 15 pages.

(56) References Cited

OTHER PUBLICATIONS

Office Action dated Dec. 8, 2009 from U.S. Appl. No. 11/715,128, 13 pages.
Office Action Response dated Aug. 13, 2009 from U.S. Appl. No. 11/715,128, 12 pages.
Office Action dated Apr. 14, 2009 from U.S. Appl. No. 11/715,128, 12 pages.
File History for U.S. Appl. No. 13/104,439, 101 pages.
Office Action Response dated Oct. 2, 2012 from U.S. Appl. No. 11/643,220, 12 pages.
Office Action dated Oct. 2, 2012 from U.S. Appl. No. 13/104,439, 19 pages.
File history for U.S. Appl. No. 11/643,220, 381 pages.
File History for U.S. Appl. No. 11/643,220, 432 pages.

\* cited by examiner

METHODS AND DEVICES FOR DETERMINATION OF ARRHYTHMIA RATE ZONE THRESHOLDS

RELATED APPLICATIONS

This application is a division of U.S. patent application Ser. No. 11/506,253 filed on Aug. 18, 2006, now U.S. Pat. No. 7,580,741 issued Aug. 25, 2009 to which Applicant claims priority under 35 U.S.C. §120, and which is incorporated herein by reference.

FIELD OF THE INVENTION

The present invention relates generally to determining rate zones for tachyarrhythmia detection and therapy.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in a region of the heart above the ventricles is denoted a supraventricular tachyarrhythmia (SVT). Atrial fibrillation and atrial flutter are examples of SVT. Both conditions are characterized by rapid, uncoordinated contractions of the atria.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmia. Ventricular tachyarrhythmia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable cardiac rhythm management (CRM) devices, including pacemakers and implantable cardioverter/defibrillators, have been used to deliver effective treatment to patients with serious cardiac arrhythmias. Cardiac rhythm management devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the CRM device must first identify the type of arrhythmia that is occurring, after which appropriate therapy may be delivered to the heart.

SUMMARY OF THE INVENTION

The present invention is directed to methods and systems used for tachyarrhythmia detection and therapy. One embodiment of the invention is directed to a method for detecting cardiac arrhythmia. Heart rate values are collected and measured. A probability function for heart rate is determined using the collected and measured heart rate values. One or more heart rate probability values are selected. One or more thresholds for arrhythmia rate zones are determined from the probability function based on the one or more probability values. For example, determining the one or more rate zone thresholds may involve determining a threshold for a lower rate limit and/or determining one or more tachyarrhythmia rate zone thresholds. Cardiac tachyarrhythmia may be detected and/or therapy delivered based on the rate zone thresholds.

In accordance with aspects of the invention, the collected and measured heart rate values comprise RR or PP intervals. The probability function is determined using the RR or PP intervals. A probability function developed using RR intervals may be used to determine one or more ventricular rate zone thresholds. A probability function developed using PP intervals may be used to determine one or more atrial rate zone thresholds.

In one implementation, the probability function comprises a cumulative density function.

The probability values may be selected by entering one or more fractional probability values via a patient-external device.

The probability function may be used as a lookup table with the one or more probability values used as indexes to the lookup table. The probability values may be input into the probability function to determine the one or more rate thresholds.

In one implementation, a number of arrhythmia rate zones may be determined based on the probability function. The probability function may involve a one dimensional probability function of ventricular rate values or a one dimensional probability of atrial rate values. In another example, the probability function may involve a two dimensional probability function of atrial rate values and ventricular rate values. Atrioventricular patterns may be identified based on the two dimensional probability function of atrial rate values and ventricular rate values. The one or more rate zone thresholds may be determined based on the two dimensional probability function.

Multiple rate thresholds respectively associated with multiple rate zones may be determined. An arrhythmia may be detected based on the multiple rate zones; and cardiac stimulation therapy delivered to treat the detected arrhythmia. For example, the cardiac stimulation therapy may involve delivery of multiple therapies, each therapy respectively associated with one of the multiple rate zones.

Another embodiment of the invention is directed to a cardiac device. The cardiac device includes sensing circuitry that senses cardiac electrical signals. Heart rate measurement circuitry measures heart rate values based on the sensed cardiac electrical signals. A memory buffer stores the measured heart rate values. A rate zone processor develops a probability function for heart rate based on the measured heart rate values and determines at least one rate zone threshold from the probability function based a heart rate probability value. The probability function may comprise a probability density function or a cumulative distribution function, for example. The at least one rate zone threshold may comprise a lower rate limit and/or may comprise one or more ventricular and/or atrial tachyarrhythmia rate zone thresholds.

The cardiac device may further include detection circuitry configured to detect arrhythmia based on the rate zone threshold and therapy circuitry configured to deliver electrical stimulation therapy to treat the arrhythmia.

In one implementation, the rate zone processor is configured to automatically select the heart rate probability. In one implementation, the cardiac device includes communication circuitry configured to receive the heart rate probability value entered via a patient-external device.

The rate zone processor may use the probability function as a lookup table to determine the rate zone threshold using the heart rate probability value as an index. The rate zone processor may solve the probability function using the heart rate probability value to determine the rate zone threshold.

In one configuration, the heart rate measurement circuitry measures intervals between cardiac beats. The rate zone processor develops the probability function based on the measured intervals.

According to one implementation, the rate zone processor may be further configured to determine a number of rate zones based on the probability function.

Another embodiment of the invention is directed to a method for determining rate zones for cardiac arrhythmia. The method includes collecting measured heart rate values. A probability function for the collected and measured heart rate values is determined. A number of rate zones for tachyarrhythmia detection is determined based on the probability function.

In one approach, the number of rate zones may be determined based a number of features of the probability function.

In one approach, the probability function is a cumulative distribution function. The number of rate zones is determined by analyzing the cumulative distribution function to identify flat portions of the cumulative distribution function.

In another approach, the probability function is a probability density function. The number of rate zones is determined by analyzing the probability density function to identify peaks of the probability density function. The number of rate zones may be updated periodically.

Another embodiment of the invention is directed to a cardiac device. The device includes sensing circuitry configured to sense cardiac electrical signals. Heart rate measurement circuitry collects measured heart rate values based on the sensed cardiac electrical signals. A rate zone processor determines a number of rate zones for tachyarrhythmia detection based on a probability function for the collected and measured heart rate values.

In one approach, the probability function is a cumulative distribution function. The rate zone processor is configured to analyze the cumulative distribution function to identify flat portions of the cumulative distribution function and to determine the number of rate zones for tachyarrhythmia detection based on the identified flat portions of the cumulative distribution function. In another approach, the probability function is a probability density function. The rate zone processor analyzes the cumulative distribution function to identify peaks of the probability density function and to determine the number of rate zones for tachyarrhythmia detection based on the identified peaks of the probability density function.

The cardiac device may also include a tachyarrhythmia detector configured to detect tachyarrhythmia based on the number of rate zones. The cardiac device may also include a therapy circuit configured to deliver multiple tachyarrhythmia therapies, each therapy associated with a particular rate zone.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
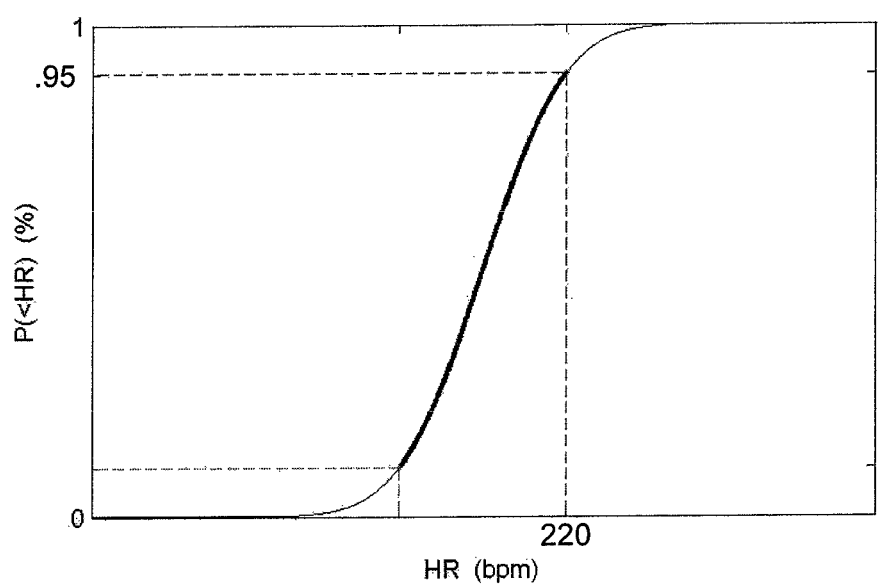
FIG. 1A is a probability function for heart rate indicating a 95% probability that the patient's heart rate will be less than or equal to 220 bpm.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Some current cardiac rhythm management (CRM) devices are capable of being programmed to have one or more tachyarrhythmia rate zones, each of which is defined by a rate threshold. When a patient's heart rate increases above a rate threshold, a tachyarrhythmia episode is detected and tachyarrhythmia therapy, such as anti-tachycardia pacing (ATP), cardioversion, and/or defibrillation may be delivered. Current CRM devices may also be programmed with a lower rate limit (LRL) for bradycardia pacing. When a patient's heart rate decreases below the LRL, the CRM device delivers pacing pulses to the heart to maintain a hemodynamically sufficient heart rate.

A physician may set the tachyarrhythmia rate thresholds and the LRL for a device at implant or may manually adjust the thresholds and/or LRL during follow-up visits to adapt to a patient's changing medical status. Manual adjustment of rate thresholds is time consuming, and, as a result, physicians may leave the thresholds set at their nominal values, producing sub-optimal tachyarrhythmia therapy. Furthermore, recent studies have shown that even when physicians attempt to manually optimize the tachyarrhythmia rate zone thresholds for a particular patient, the CRM device still may not deliver optimal therapy.

The present invention is directed to methods and systems for automatically or semi-automatically determining the number of tachyarrhythmia rate zones, tachyarrhythmia rate zone thresholds, and/or the LRL for a CRM device. According to various embodiments, determination of the number of rate zones and/or rate zone thresholds and the LRL is accomplished based upon a probability function for heart rate. The probability function predicts the likelihood of future heart rates based on previously measured heart rate values. For example, a probability function for heart rate may be determined using a set of heart rate values that have been periodically measured and stored. In general, a probability function provides the probability that a variable, which in this application is heart rate, will take on a certain value. As related to heart rate, the probability function can be used to determine the probability that the patient's heart rate will take on a value greater than or less than a certain value. In a specific example, based on a probability function developed from a particular set of collected and measured heart rate values (illustrated in FIG. 1A), the probability that a patient will have a heart rate less than 220 bpm is 0.95 which may be expressed as a 95% probability. According to various embodiments, rate zone thresholds are established from one or more selected probability values using a probability function.

Figure 1B:
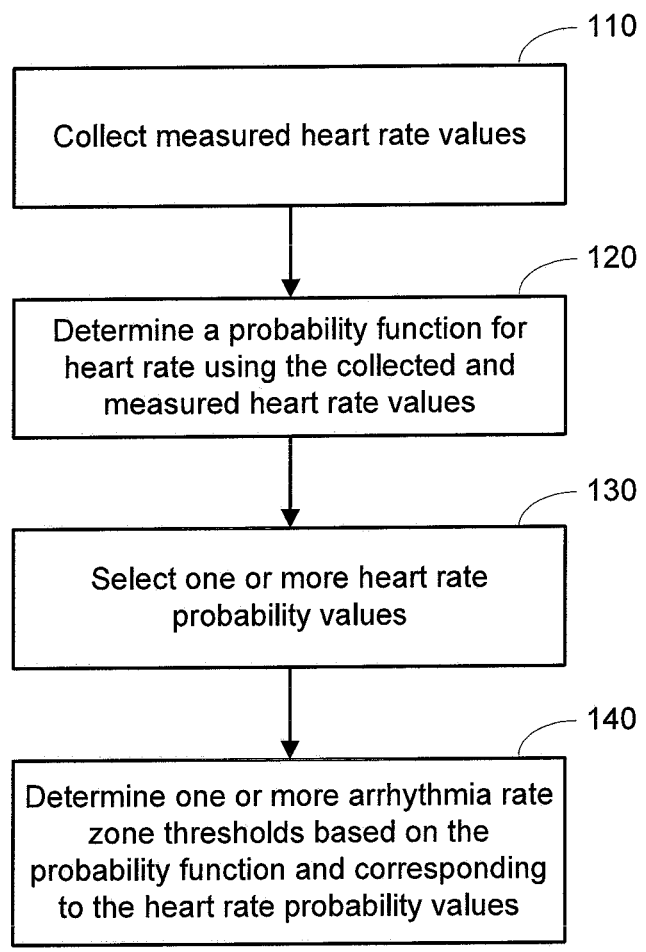
FIG. 1B is a flow chart illustrating a method for determining arrhythmia rate zones in accordance with embodiments of the invention.

A method for determining arrhythmia rate zone thresholds is illustrated by the flowchart of FIG. 1B. A set of measured heart rate values is collected 110, such as in a buffer in the memory of a CRM device. A probability function for heart rate is determined 120 based on the set of collected and measured heart rate values. One or more heart rate probability values are selected 130. For example, the heart rate probability values may be pre-programmed into a device, may be selected automatically by the device, or may be selected by a physician via an external programmer. One or more arrhythmia rate thresholds corresponding to the selected probability values are determined 140 based on the probability function.

According to various aspects of the invention, the rate zone thresholds determined using the processes described herein may be atrial rate zone thresholds for atrial rate zones used for detection and therapy for atrial arrhythmias or may be ventricular rate zone thresholds for ventricular rate zones used for detection and therapy for ventricular arrhythmias. For example, a probability function useful for determining ventricular rate zones may be developed using measured and collected ventricular rate values, or intervals between ventricular beats (R-R intervals). A probability function useful for determining atrial rate zones may be developed using measured and collected atrial rate values or intervals between atrial beats (P-P intervals). In other implementations, the probability function may be developed using intervals between ventricular beats and atrial beats (RP intervals) and/or intervals between atrial beats and ventricular beats (PR intervals).

The processes described herein may be used for automatic, semi-automatic, or manual initialization and/or adaptation of the a patient's tachyarrhythmia rate zone thresholds and/or LRL based on a probability function developed using the distribution of heart rates the patient has experienced in the past. In some embodiments, the number of rate zones may be determined based on the probability function. Automatic, semi-automatic, or manual determination of rate zone thresholds may be incorporated into CRM devices for delivery of appropriate, adaptable tachyarrhythmia therapy, wherein the device learns over time the appropriate number and thresholds for tachyarrhythmia rate zones for a particular patient. Additionally or alternatively, the processes described herein may be incorporated into CRM devices that include pacing functionality for adjusting a lower rate limit (LRL) for pacing when a currently used LRL is determined to be suboptimal.

Figure 2:
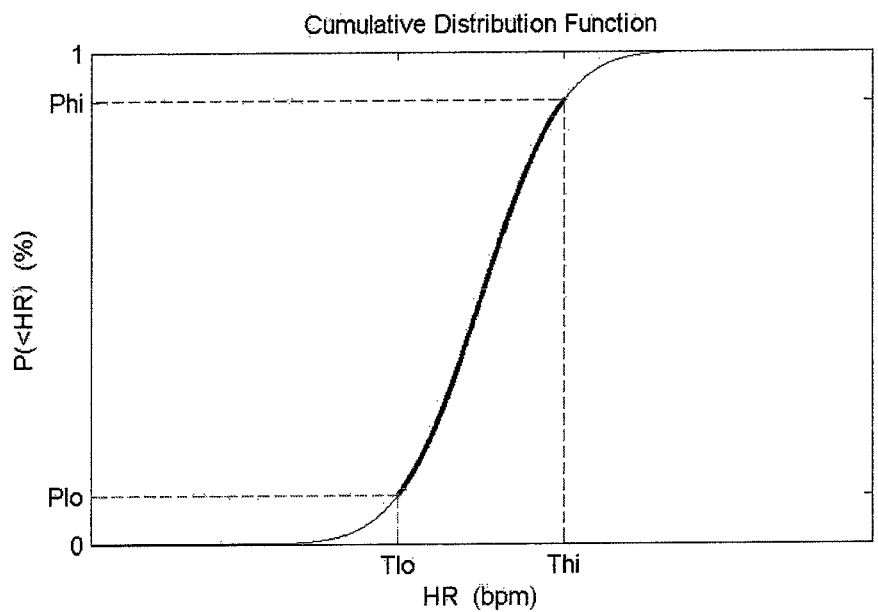
FIG. 2 illustrates a cumulative distribution function of heart rate developed based on measurements of the patient's average heart rates that may be used to determine the number and/or thresholds for rate zones in accordance with embodiments of the invention.

In one embodiment of the invention the probability function is a cumulative distribution function (CDF) created from periodic measurements of the patient's heart rate. In one example, the CDF, illustrated in FIG. 2, is developed based on measurements of the patient's average heart rate taken every T minutes, where T may be equal to about one hour, about 65 minutes, or other appropriate value. The average heart rate may be computed using a sample of about 10 beats or intervals, for example. Thus, according to this process, every T minutes, an average heart rate is computed, based on a predetermined number of beats or intervals. In this example, the heart rate measurements are stored in a buffer. If the buffer is full, as a new average heart rate measurement comes into the buffer, the oldest measurement is erased. The measurements in the buffer include average values obtained from intrinsic rhythm measurements, including measurements taken during tachyarrhythmia or bradyarrhythmia episodes. An intrinsic bradyarrhythmia episode can occur if the LRL is set too low.

In another example, the CDF is developed based on measurements of the time intervals between successive heart beats, thereby creating one new heart rate measurement every heart beat. In this example, the CDF may be created every T minutes, every T hours or every T days. The CDF is composed of all the time intervals that occur within those T minutes, hours or days so that short tachyarrhythmia episodes are not missed or averaged out.

Figure 3:
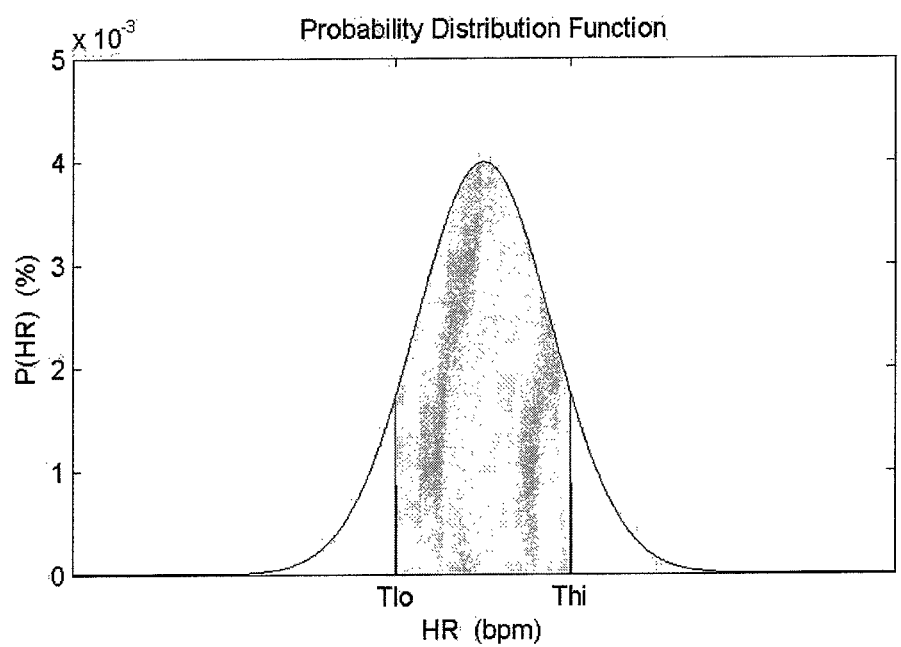
FIG. 3 illustrates a probability density function of heart rate developed based on measurements of the patient's heart rate that may be used to determine the number and/or threshold values for rate zones in accordance with embodiments of the invention.

A CDF, as illustrated in FIG. 2, may be updated every T minutes, for example, using the current measurements stored in the buffer. FIG. 2 illustrates an idealized case where the average heart rate measurements are normally distributed. Alternatively, the probability function used to determine the rate zone thresholds may be a probability density function (PDF) as illustrated in FIG. 3. In FIGS. 2 and 3, the horizontal axes represent the range of measured heart rate values. In FIG. 2, the vertical axis is the fraction of measurements stored in the buffer that are less than a particular heart rate value. In FIG. 3, the vertical axis is the fraction of measurements stored in the buffer that are equal to a particular heart rate value. In the example provided below, determination of rate zone thresholds is illustrated using the CDF, although the PDF (or other probability functions) may alternatively be used.

With reference to FIG. 2, there is a probability value, $P_{hi}$, corresponding to a fraction of heart rate measurements that are less than a particular heart rate value, $T_{hi}$. Similarly, there is a probability value, $P_{lo}$, corresponding to a fraction of heart rate measurements that are less than a particular heart rate value, $T_{lo}$. Heart rate values within the range $T_{lo}$-$T_{hi}$ are considered to be normal sinus rhythm (NSR). Heart rates greater than $T_{hi}$ are considered tachyarrhythmic, while heart rates less than $T_{lo}$ are considered bradyarrhythmic.

At implant or at any clinic visit, rather than directly specifying heart rate values for the rate zone thresholds or LRL, a physician may instead select $P_{hi}$ and/or $P_{lo}$. $P_{hi}$ is used to specify the tachyarrhythmia threshold rate value $T_{hi}$. $P_{lo}$ is used to specify the bradyarrhythmia threshold value, or lower rate limit (LRL) $T_{lo}$. In various embodiments, $P_{hi}$ and/or $P_{lo}$ may also be pre-programmed into the device as nominal values or may be selected by the physician at the time of implant or subsequent to implant. Based on the values of $P_{hi}$ and/or $P_{lo}$, the device uses the CDF to determine the corresponding values for $T_{hi}$ and/or $T_{lo}$ for that particular patient. Thus, the probability function serves as a functional "look-up table" with the probability values as indexes for determining values for the tachyarrhythmia rate zone threshold, $T_{hi}$, and/or the LRL, $T_{lo}$, that correspond to the selected values of $P_{hi}$ and $P_{lo}$, respectively. A rate threshold may be determined by inputting a probability value into the probability function equation and solving the equation to determine the rate threshold.

Use of a probability function and specification of probability values rather than rates to determine rate thresholds allows the rate zone thresholds to adapt over time. For example, if a physician selects a particular heart rate as a rate zone threshold, that rate zone threshold is static over time. However, when the rate zone threshold is specified as a probability value, rather than a static heart rate, the rate of the rate zone threshold is dynamic. As the set of measured values used to develop the probability function shifts, the probability value stays constant but the threshold rate corresponding to the probability value changes along with the probability function.

The use of the probability function in determining rate zone thresholds allows the physician to more easily compare the effects of tachyarrhythmia rate zone thresholds across patients. For example, a relatively low tachyarrhythmia rate threshold may be optimum for an inactive patient but can be severely inadequate for an active patient. As a specific example, consider an elderly, inactive patient having NSR that varies from 60-90 bpm. A tachyarrhythmia rate zone threshold of 130 may be adequate for this patient. However, consider a patient whose NSR varies from 60-150 bpm. Setting a tachyarrhythmia rate zone threshold for this patient at 130 may result in frequent delivery of inappropriate anti-tachyarrhythmia therapy.

However, using the principles of the invention, selecting a probability value of 99% would yield an appropriate tachyarrhythmia rate zone threshold value for both of these patients. A $P_{hi}$ selected as 99.9% will classify as tachyarrhythmic the highest 0.1% of a patient's heart rate measurements, regardless of whether the patient's NSR ranges from 60-90 bpm or 60-150 bpm.

According to some embodiments, multiple rate zones may be specified using the processes described herein. In one example, the physician could specify multiple values of $P_{hi}$, such as $P_{hi1}$=99.5%, $P_{hi2}$=99.7%, and $P_{hi3}$=99.9%. The device determines values for $T_{hi1}$, $T_{hi2}$, $T_{hi3}$, respectively corresponding to $P_{hi1}$, $P_{hi2}$, and $P_{hi3}$ such as through the use of a CDF or a PDF. A lowest tachyarrhythmia rate zone (VT-1) would span the range of rates $T_{hi1}$-$T_{hi2}$, the next tachyarrhythmia rate zone (VT-2) would span the range $T_{hi2}$-$T_{hi3}$, and the fibrillation rate zone (VF) would include rates greater than $T_{hi3}$.

Some patients require only one tachyarrhythmia rate zone while other patients may need two or more. Multiple rate zones may be advantageous for patients that experience several types of arrhythmias, wherein each arrhythmias occurs at a different rate. Different types of arrhythmias may be best treated using different therapy schemes. Some embodiments of the invention are directed to methods and devices for determining the number of tachyarrhythmia rate zones for a particular patient.

Figure 4:
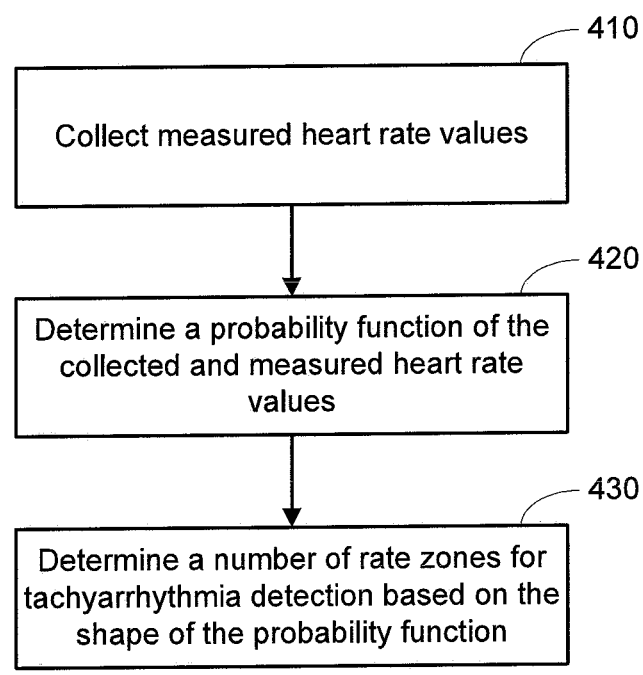
FIG. 4 is a flow chart that illustrates a method for determining the number of rate zones used for tachyarrhythmia detection and/or therapy in accordance with embodiments of the invention.

As illustrated by the flow chart of FIG. 4, the number of rate zones used for tachyarrhythmia detection and/or therapy may be determined based on a probability function for heart rate. A set of measured heart rate values is collected 410. The probability function for heart rate is developed 420 using the set of collected and measured heart rate values. The number of rate zones for arrhythmia detection is determined 430 based on the shape of the probability function.

Figure 5:
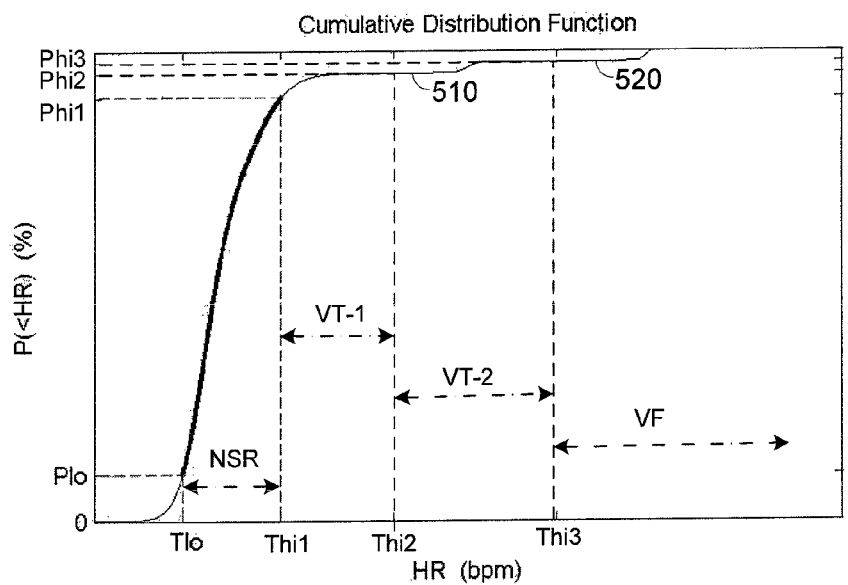
FIG. 5 illustrates a cumulative distribution function that may be used for determining the number of rate zones for tachyarrhythmia detection and/or therapy in accordance with embodiments of the invention.
Figure 6:
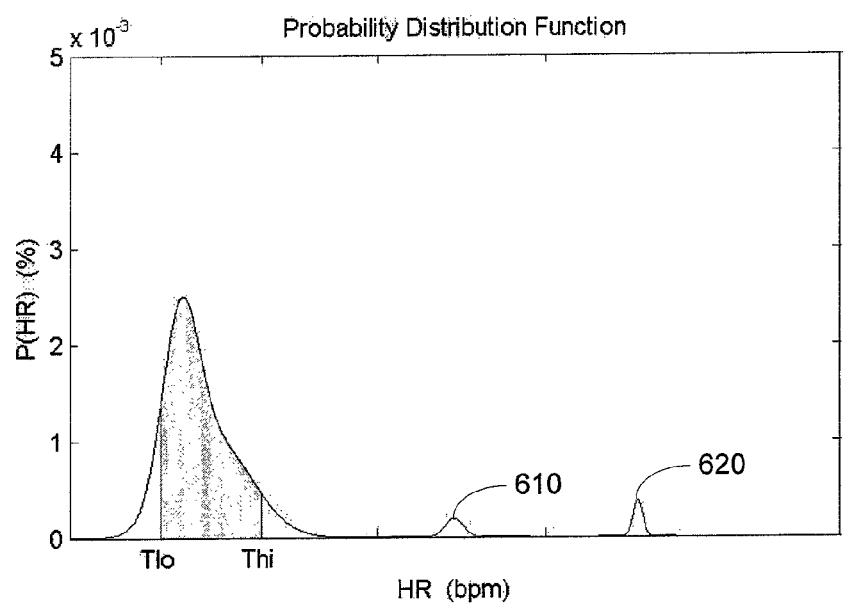
FIG. 6 illustrates a probability density function that may be used for determining the number of rate zones for tachyarrhythmia detection and/or therapy in accordance with embodiments of the invention.

FIGS. 5 and 6 illustrate determining the number of rate zones based on the shape of the probability function. FIG. 5 illustrates the process based on a CDF with FIG. 6 showing a corresponding PDF. The CDF of FIG. 5 exhibits two relatively flat portions 510, 520. The flat portions 510, 520 indicate separation between peaks 610, 620 of the PDF shown in FIG. 6. The number of the flat portions 510, 520 of the CDF (FIG. 5) or the number of peaks 610, 620 of the PDF (FIG. 6) may be used to determine the number of rate zones needed for the patient. For example, the CDF shown in FIG. 5 indicates that tachyarrhythmia detection and/or therapy may be enhanced by using two additional rate zone thresholds. A first rate zone is associated with the fraction of measured rates corresponding to $P_{hi1}$, a second rate zone is indicated by the first flat portion 510, the first flat portion associated with the fraction of measured rates corresponding to $P_{hi2}$, and a third rate zone indicated by the second flat portion 520 associated with the fraction of measured rates corresponding to $P_{hi3}$. Threshold values, $T_{hi1}$, $T_{hi2}$, and $T_{hi3}$, respectively associated with $P_{hi1}$, $P_{hi2}$, and $P_{hi3}$, are selected as the threshold values for a first rate zone 1, VT-1, a second rate zone, VT-2, and a third rate zone, VF.

After detection of a tachyarrhythmia episode by use of the rate zones VT-1, VT-2, and VF, an appropriate therapy may be delivered to terminate the arrhythmia. For example, a first type of therapy may be delivered to treat tachyarrhythmia episodes having rates that fall within rate zone VT-1, a second type of therapy may be delivered to treat tachyarrhythmia episodes that fall within rate zone VT-2, and a third type of therapy may be delivered to treat tachyarrhythmia episodes that fall within rate zone VF.

As previously discussed, the processes for determining the tachyarrhythmia rate zone threshold values, the LRL, and/or the number of tachyarrhythmia rate zones based on a probability function of heart rate values may be implemented fully automatically, semi-automatically, or manually. The tachyarrhythmia rate zones determined by the processes described herein may be used by a CRM device to detect and treat ventricular or atrial tachyarrhythmias.

Figure 7:
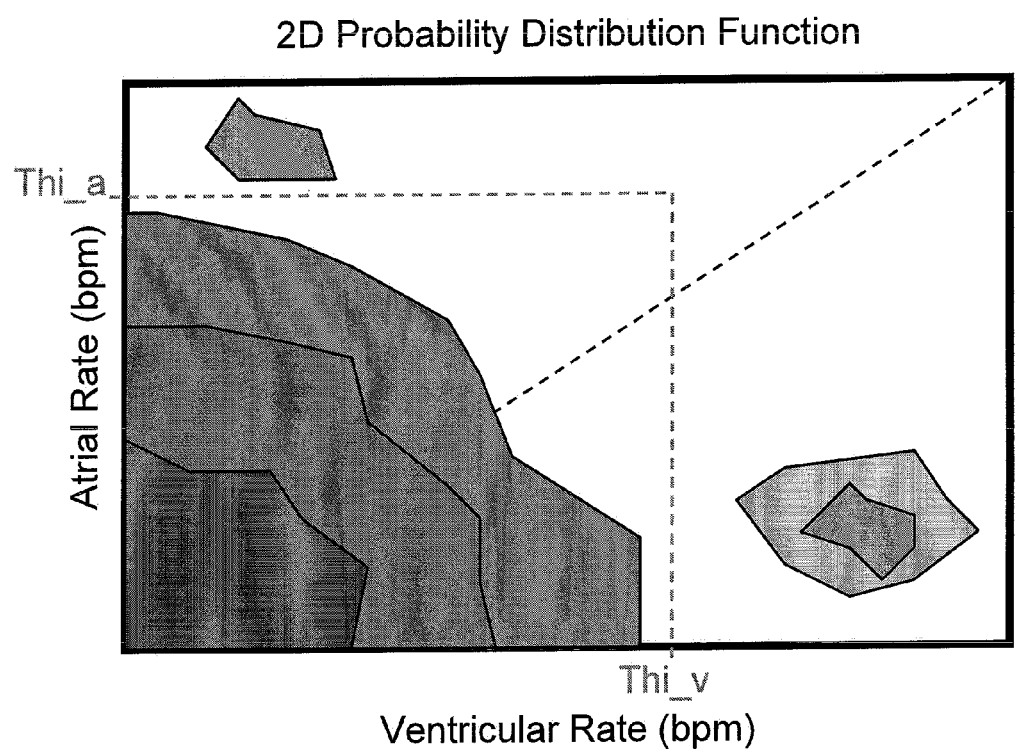
FIG. 7 illustrates a two dimensional probability density function that may be used to determine the number and/or thresholds for rate zones and/or LRL in accordance with embodiments of the invention.

In one embodiment, the CRM device may use a multi-dimensional CDF for determination of the number and/or threshold values of rate zones. For example, the CRM device may measure store both atrial and ventricular heart rates. From these values, a two dimensional CDF or PDF can be developed, with one dimension representing the atrial heart rate and a second dimension representing the ventricular rate. A two-dimensional PDF is graphically illustrated in FIG. 7 wherein the shading is used to indicate probability values of the PDF. The two dimensional PDF may be used to incorporate trends in the atrial rate into the automated choice of tachyarrhythmia rate zone thresholds and the LRL. For example, as illustrated by FIG. 7, the rate zone threshold may be multi-dimensional, having an atrial threshold, $T_{hi\_a}$, and a ventricular threshold, $T_{hi\_v}$. Tachyarrhythmia is detected, and therapy may be delivered, based on both the atrial and ventricular thresholds. The two dimensional PDF may also be used to determine a number of the rate zones for tachyarrhythmia detection. As in the one-dimensional case, the shape of the two dimensional PDF may be used to determine the number of rate zones that are optimal for a particular patient. The use of a two dimensional PDF based on both atrial and ventricular rates is particularly advantageous for patients suffering from chronic atrial tachyarrhythmia where high atrial rhythms affect the patient's ventricular rate.

Figure 8:
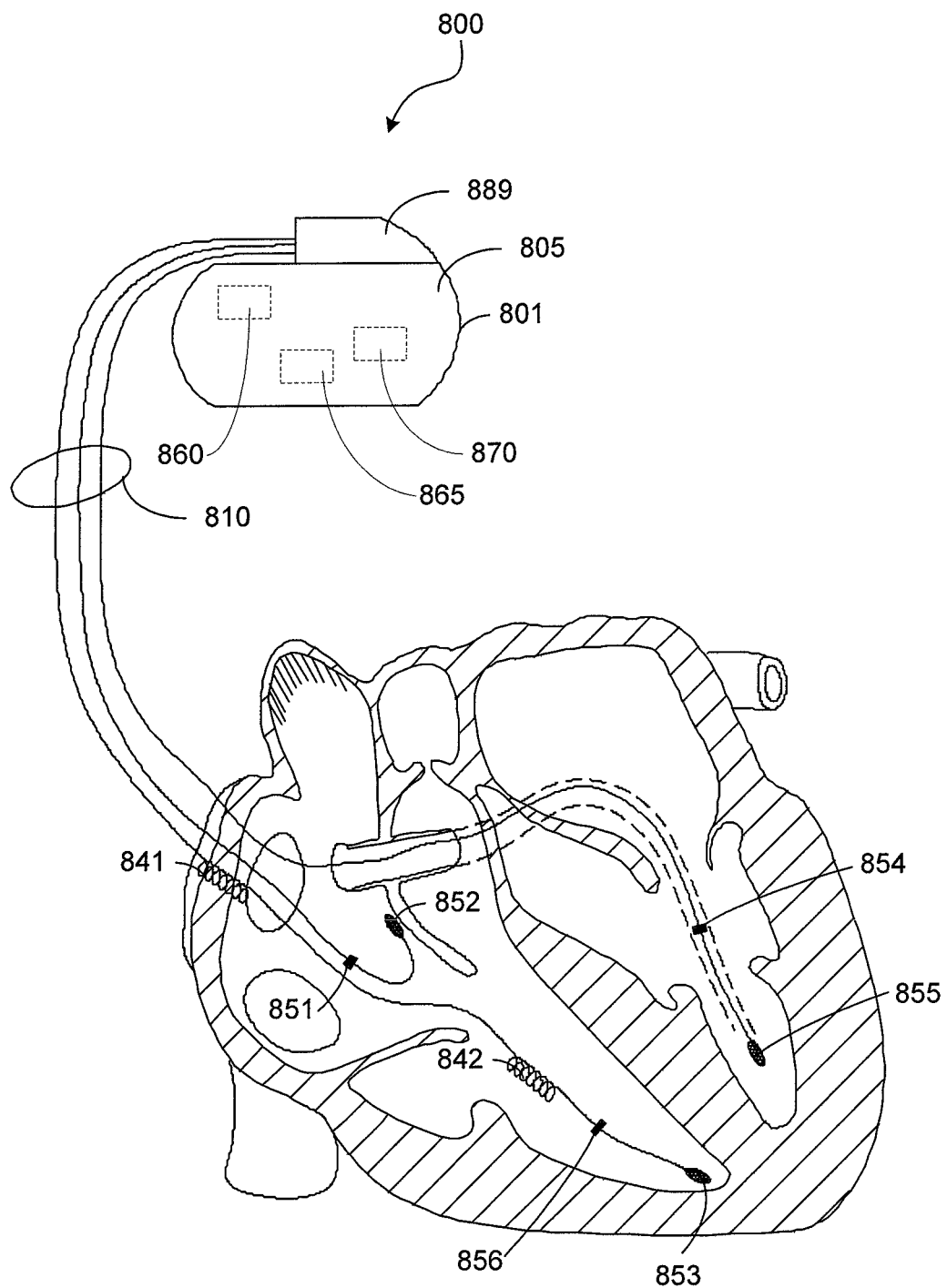
FIG. 8 is a partial view of a cardiac rhythm management device that may be used for determination of rate zones in accordance with embodiments of the invention.

FIG. 8 illustrates a view of a CRM device 800 incorporating circuitry capable of implementing processes for determining the number of tachyarrhythmia rate zones, tachyarrhythmia rate zone thresholds, and/or LRL based on a probability function of heart rate as described herein. The CRM device 800 includes circuitry enclosed within an implantable housing 801 and electrically coupled to an intracardiac lead system 810.

Portions of the intracardiac lead system 810 are inserted into the patient's heart. The lead system 810 includes cardiac pace/sense electrodes 851-856 positioned in, on, or about one or more heart chambers for sensing electrical signals from the patient's heart and/or delivering pacing pulses to the heart. The intracardiac sense/pace electrodes 851-856, such as those illustrated in FIG. 7, may be used to sense and/or pace one or more chambers of the heart, including the left ventricle, the right ventricle, the left atrium and/or the right atrium. The lead system 810 also includes defibrillation coils 841, 842. The CRM circuitry controls electrical stimulation delivered via the electrodes 841, 842, 851-856. The electrical stimulation may be delivered in the form of ATP or cardioversion/defibrillation shocks to interrupt tachyarrhythmic episodes. The electrical stimulation may be delivered in the form of relatively low energy pacing pulses to ensure that the heart beats at a hemodynamically sufficient rate.

The lead system 810 may include a left ventricular lead system incorporating electrodes 854 and 855 positioned within the coronary venous system proximate the left ventricle. Stimulating the ventricle at multiple locations in the left ventricle or at a single selected location may provide for increased cardiac output in a patients suffering from congestive heart failure (CHF), for example, and/or may provide for other benefits.

Portions of the housing 801 of the CRM device 800 may optionally serve as one or multiple can or indifferent electrodes. The housing 801 is illustrated as incorporating a header 889 that may be configured to facilitate removable attachment between one or more leads of the lead system 810 and the housing 801. The housing 801 of the CRM device 800 may include one or more can electrodes that may be used for pacing and/or cardioversion/defibrillation.

The CRM device illustrated in FIG. 8 includes circuitry for measuring heart rate 860, a memory for storing heart rate measurements 865, and circuitry 870 for determining the number and/or threshold values for one or more tachyarrhythmia rate zones based on a probability function for heart rate. The heart rate measurement circuitry 860, memory 865, and rate zone circuitry 870 may also be used to determine the LRL for bradyarrhythmia pacing as described herein.

Communications circuitry is disposed within the housing 801 for facilitating communication between the CRM device 800 and a patient-external device, such as an external programmer or advanced patient management (APM) system.

Determination of the number of rate zones and/or rate zone thresholds may be performed automatically by the device or may be performed semi-automatically using a probability value received from a physician via the patient-external programmer.

In an example of semi-automatic operation, the CRM device 800 may periodically measure heart rate and collect heart rate measurements in a memory buffer. The CRM device 800 then develops a probability function of heart rate based on the collected and measured heart rate measurements. Via the programmer, a physician can enter a probability value used for determining a rate zone threshold. For example, the physician may specify that the rate zone threshold be set at value corresponding to a fraction of the set of measured and collected heart rate measurements, such as 95%. The CRM device 800 selects the heart rate value from the probability function that is greater than 95% of the measurements included in buffer as the rate zone threshold.

Figure 9:
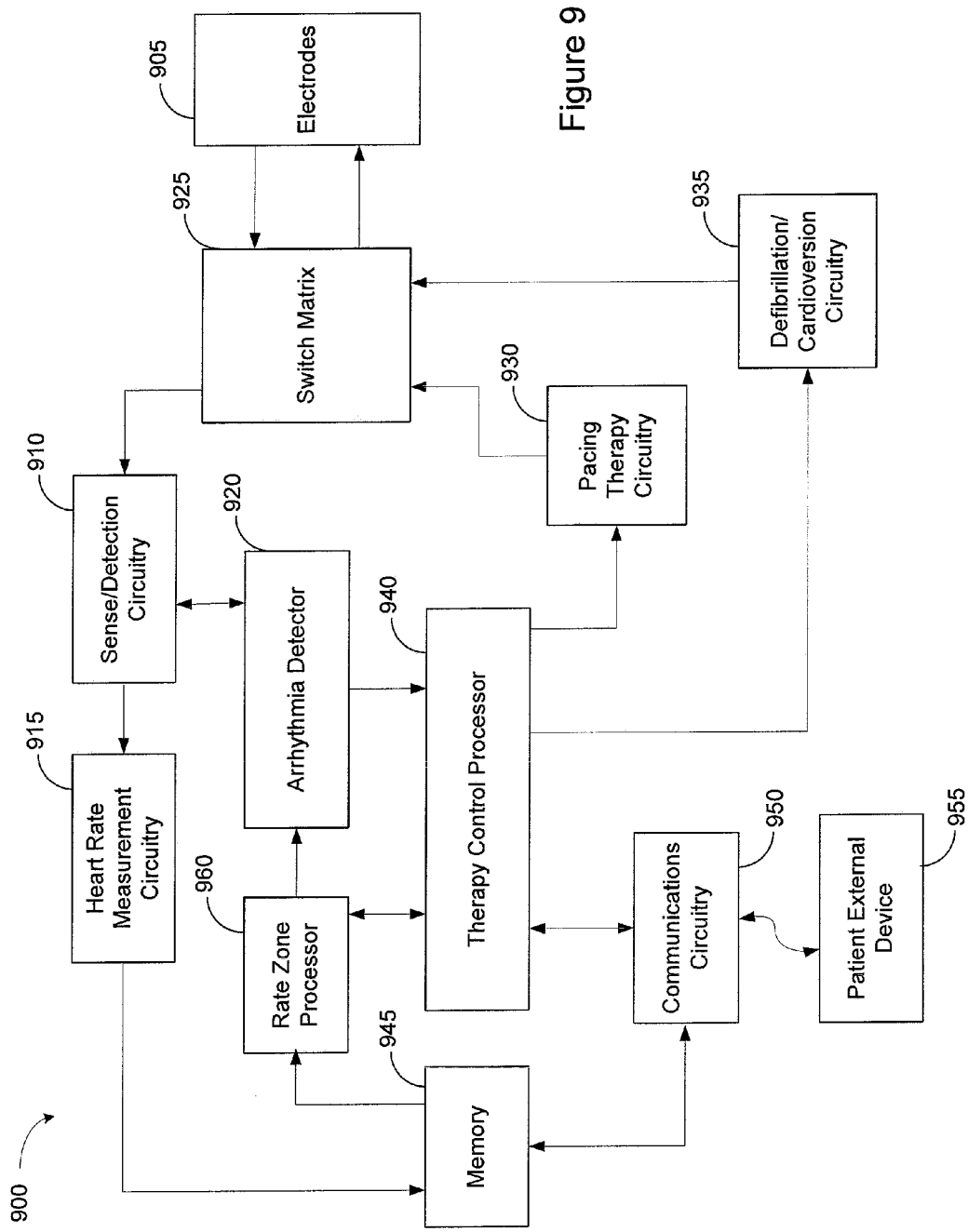
FIG. 9 is a block diagram of a cardiac rhythm management device that may be used to determine the number and/or thresholds for rate zones in accordance with embodiments of the invention.

FIG. 9 is a block diagram of a CRM device 900 incorporating circuitry for determining the number and/or thresholds for rate zones in accordance with embodiments of the invention. The CRM device 900 includes pacing therapy circuitry 930 that delivers pacing pulses to a heart. The CRM device 900 may optionally include defibrillation/cardioversion circuitry 935 configured to deliver high energy defibrillation or cardioversion stimulation to the heart for terminating dangerous tachyarrhythmias.

The pacing and/or defibrillation pulses may be delivered via multiple cardiac electrodes 905 disposed at multiple locations within a heart. The electrodes 905 are coupled to switch matrix 925 circuitry used to selectively couple electrodes 905 of various pacing vectors to sensing and therapy circuitry 910, 930, 935.

The sensing/detection circuitry 910 in cooperation with sensing electrodes 905 detect electrical signals produced by heart. From the heart's sensed electrical signals, the heart rate measurement circuitry 915 periodically, e.g., about every hour or about every 65 minutes, determines the average heart rate or average interval between beats. For example, the heart rate measurement circuitry 915 may measure the atrial rate or P-P intervals and/or may measure the ventricular rate or R-R intervals. Measurements of heart rate (or heart rate interval measurements) are stored in a circular buffer in the memory 945.

Periodically, the rate zone processor 960 accesses the memory buffer and calculates a probability function for heart rate from the measurement values stored in the buffer. The rate zone processor 960 may determine the number of rate zones that are appropriate to enhance tachyarrhythmia detection and/or therapy delivered to the patient.

A probability value used for determining a rate zone threshold may be determined either by the CRM device 900 or may be entered by a physician from a patient external device 955 via communications circuitry 950. The rate zone processor 960 uses the probability value determine the rate zone threshold value based on the probability function. In certain implementations, the rate zone processor 960 may also determine or modify the LRL used for pacing based on the probability function.

The rate zone processor 960 may determine one or more rate zone thresholds, may determine a LRL, and may determine the number of rate zones. The arrhythmia detector 920 uses the rate zone thresholds for detecting arrhythmia. For example, the arrhythmia detector may compare a current heart rate to the rate zone thresholds and may determine that tachyarrhythmia is occurring if the heart rate exceeds a rate zone threshold. If tachyarrhythmia occurs, the therapy control processor 940 may control the delivery of therapy to mitigate the tachyarrhythmia. If The therapy control processor may have the capability to delivery multiple types of therapies, involving anti-tachyarrhythmia pacing (ATP), cardioversion and/or defibrillation. These multiple types or therapies may be associated respectively with rate zones. Where multiple therapies respectively associated with multiple rate zones are used, the therapy control processor 940 controls delivery of a therapy associated with the particular rate zone of the arrhythmia. The therapy control processor may also control delivery of pacing pulses to maintain pacing above the LRL.

An cardiac device according to the present invention may include one or more of the features, structures, methods, or combinations thereof described herein. For example, a cardiac device may be implemented to include one or more of the advantageous features and/or processes described. It is intended that such a implanted, partially implanted, or patient-external device need not include all of the features described herein, but may be implemented to include selected features that provide for useful structures and/or functionality.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of delivering cardiac therapy, comprising:
   measuring heart rate values;
   determining a probability function for the measured heart rate values;
   determining a number of heart rate zones based on the probability function, wherein the number of heart rate zones are periodically updated; and
   delivering the cardiac therapy via a cardiac therapy device based on the rate zones.

2. The method of claim 1, wherein determining the number of rate zones comprises:
   detecting one or more features of the probability function; and
   determining the number of rate zones based on a number of the one or more features.

3. The method of claim 1, wherein:
   the probability function comprises a cumulative distribution function; and
   determining the number of rate zones comprises analyzing the cumulative distribution function to identify flat portions of the cumulative distribution function.

4. The method of claim 1, wherein:
   the probability function comprises a probability density function; and
   determining the number of rate zones comprises analyzing the probability density function to identify peaks of the probability density function.

5. The method of claim 1, further comprising determining one or more thresholds of the rate zones.

6. The method of claim 1, wherein the number of rate zones comprises only one rate zone before or after being updated.

7. The method of claim 1, wherein the number of rate zones comprises two or more rate zones.

8. The method of claim 1, wherein determining the number of rate zones comprises determining the number of rate zones fully automatically in the cardiac therapy device.

9. The method of claim 1, wherein the cardiac therapy device comprises an implantable cardiac therapy device.

10. The method of claim 1, wherein delivering the cardiac therapy via a cardiac therapy device comprises delivering multiple tachyarrhythmia therapies, each therapy associated with a particular rate zone.

11. A cardiac device, comprising:
    sensing circuitry configured to sense cardiac electrical signals;
    heart rate measurement circuitry coupled to the sensing circuitry and configured to measure heart rate values based on the sensed cardiac electrical signals; and
    a rate zone processor configured to determine a number of rate zones based on a probability function for the measured heart rate values, wherein the number of heart rate zones are periodically updated.

12. The device of claim 11, wherein:
    the probability function comprises a cumulative distribution function; and
    the rate zone processor is configured to analyze the cumulative distribution function to identify flat portions of the cumulative distribution function and to determine the number of rate zones for tachyarrhythmia detection based on the identified flat portions of the cumulative distribution function.

13. The device of claim 11, wherein:
    the probability function comprises a probability density function; and
    the rate zone processor is configured to analyze the probability density function to identify peaks of the probability density function and to determine the number of rate zones for tachyarrhythmia detection based on the identified peaks of the probability density function.

14. The device of claim 11, further comprising a tachyarrhythmia detector configured to detect tachyarrhythmia by comparing a rate of the tachyarrhythmia to one or more of the rate zones.

15. The device of claim 11, further comprising a therapy circuit configured to deliver multiple tachyarrhythmia therapies, each therapy associated with a particular rate zone.

16. A cardiac therapy system, comprising:
    sensing circuitry configured to sense cardiac electrical signals;
    heart rate measurement circuitry coupled to the sensing circuitry and configured to measure heart rate values based on the sensed cardiac electrical signals; and
    means for determining a number of heart rate zones based on a probability function for the measured heart rate values, wherein the number of heart rate zones are periodically updated.

17. The cardiac therapy system of claim 16, further comprising therapy circuitry for delivering multiple therapies, each therapy associated with a particular rate zone.

18. The cardiac therapy system of claim 16, wherein:
    the probability function comprises a cumulative distribution function; and
    further comprising a rate zone processor for determining the number of rate zones by analyzing the cumulative distribution function to identify flat portions of the cumulative distribution function.

19. The cardiac therapy system of claim 16, wherein:
    the probability function comprises a probability density function; and
    further comprising a rate zone processor for determining the number of rate zones by analyzing the probability density function to identify peaks of the probability density function.

* * * * *